United States Patent
Poezevara et al.

(10) Patent No.: US 6,738,665 B2
(45) Date of Patent: May 18, 2004

(54) DETECTION OF LATE ATRIAL EXTRASYSTOLES IN AN ACTIVE IMPLANTABLE MEDICAL DEVICE SUCH AS PACEMAKER DEFIBRILLATOR, CARDIOVERTOR AND/OR MULTISITE DEVICE

(75) Inventors: Yann Poezevara, Courcouronne (FR); Jean-Luc Bonnet, Olivet (FR)

(73) Assignee: ELA Medical S.A., Montrouge (FR)

( * ) Notice: Subject to any disclaimer, the term of this patent is extended or adjusted under 35 U.S.C. 154(b) by 157 days.

(21) Appl. No.: 09/875,849

(22) Filed: Jun. 5, 2001

(65) Prior Publication Data

US 2002/0010493 A1 Jan. 24, 2002

(30) Foreign Application Priority Data

Jun. 5, 2000 (FR) .............................. 00 07158

(51) Int. Cl.$^7$ ................................ A61N 1/36
(52) U.S. Cl. .......................................... 607/9
(58) Field of Search ...................... 607/5, 9, 15, 14

(56) References Cited

U.S. PATENT DOCUMENTS

| | | | | |
|---|---|---|---|---|
| 3,857,399 A | * | 12/1974 | Zacouto | 607/9 |
| 5,271,394 A | * | 12/1993 | Girodo et al. | 607/15 |
| 5,312,451 A | * | 5/1994 | Limousin et al. | 607/15 |
| 5,480,413 A | * | 1/1996 | Greenhut et al. | 607/14 |
| 5,814,085 A | * | 9/1998 | Hill | 607/14 |
| 5,938,687 A | | 8/1999 | Bouhour et al. | 607/15 |
| 5,978,708 A | * | 11/1999 | Bonnet et al. | 607/14 |
| 6,134,469 A | * | 10/2000 | Wietholt | 607/14 |
| 6,263,242 B1 | * | 7/2001 | Mika et al. | 607/9 |
| 6,311,088 B1 | * | 10/2001 | Betzold et al. | 607/14 |
| 6,484,058 B1 | * | 11/2002 | Williams et al. | 607/14 |
| 2002/0082653 A1 | * | 6/2002 | Stahmann et al. | 607/9 |

FOREIGN PATENT DOCUMENTS

| | | | |
|---|---|---|---|
| EP | 0 885 626 | 12/1998 | A61N/1/362 |
| WO | 99 65564 | 12/1999 | A61N/1/362 |

* cited by examiner

*Primary Examiner*—Angela D. Sykes
*Assistant Examiner*—Joseph S. Machuga
(74) *Attorney, Agent, or Firm*—Orrick, Herrington & Sutcliffe LLP

(57) ABSTRACT

An active implantable medical device, such as a pacemaker, defibrillator, cardiovertor and/or a multisite device, having an improved detection of late atrial extrasystoles. The device detects atrial events (EvtA); applies a first window forming a relative atrial refractory period (DARRP) for discriminating (filtering) atrial extrasystoles of an early or average prematurity, and reacts to a variation of the sinusal atrial rate by certain control algorithms. It also applies the detected atrial events to a second window (DLE), distinct from the first window and of longer duration, for the discrimination of the atrial extrasystoles having a low prematurity, called late extrasystoles. The duration of the second window is a variable duration, defined as a fraction of the current average atrial interval (AAI). Further, the second window is used to inhibit temporarily any reaction to a variation of the sinusal atrial rate, in the event of detection of an atrial event inside the second window.

7 Claims, 3 Drawing Sheets

| | Cycle 1 | Cycle 2 | Cycle 3 | Cycle 4 | Cycle 5 | Cycle 6 | Cycle 7 |
|---|---|---|---|---|---|---|---|
| COUPLING INTERVAL FOR ATRIAL DETECTION | 900 | 900 | 900 | 600 | 900 | 900 | 900 |
| AAI | | 900 | 900 | 900 | 600 | 900 | 900 |
| VALUE OF DLE | | 737 | 737 | 737 | 550 | 737 | 737 |
| ALGORITHM | | Active | Active | Inactive | Active | Active | Active |

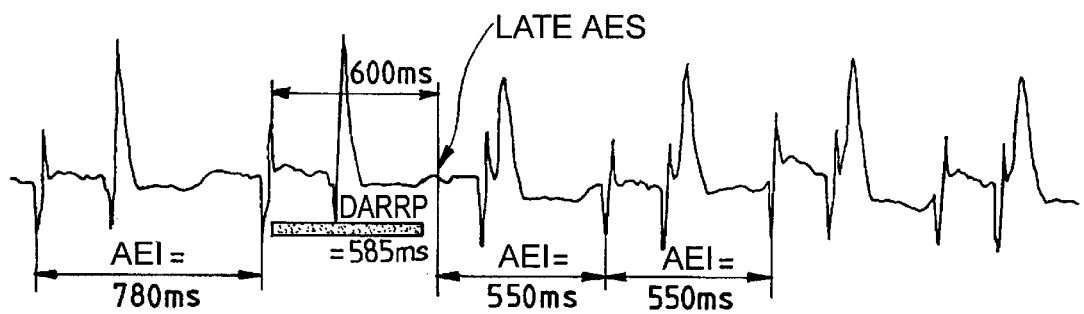
FIG_1
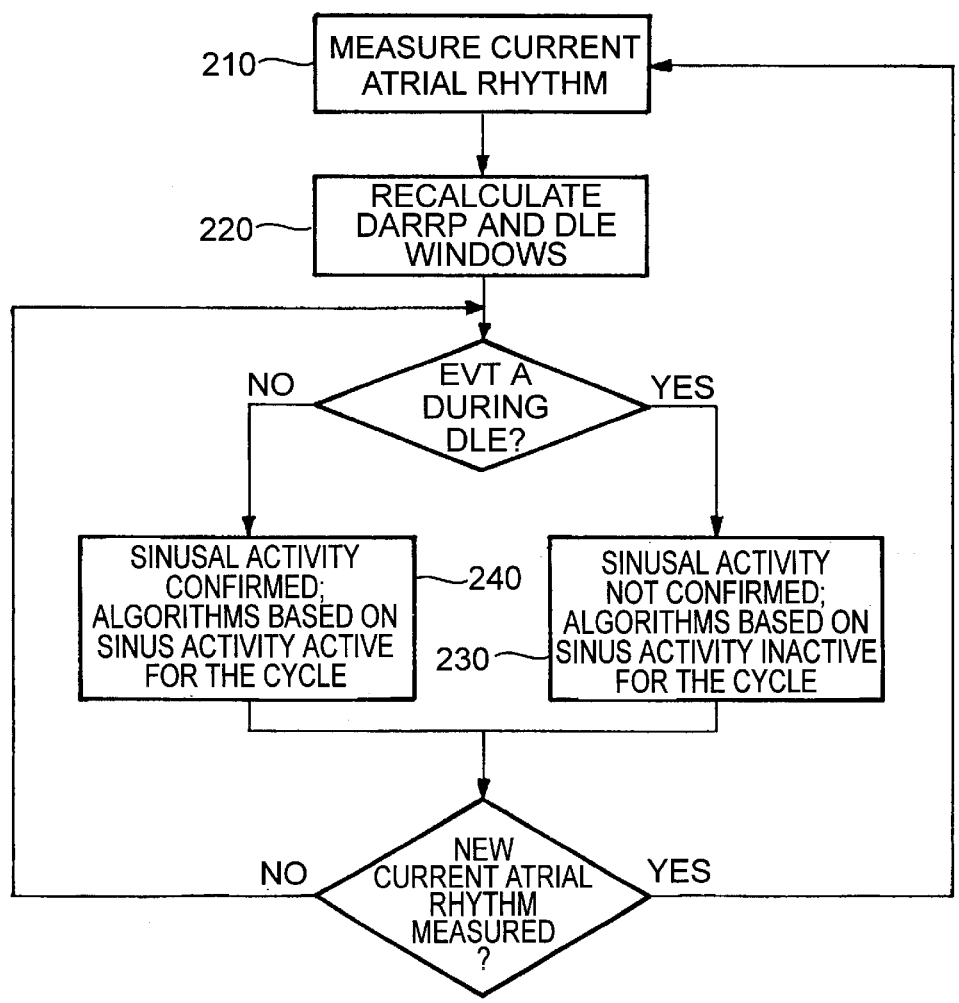
FIG_2

FIG_3
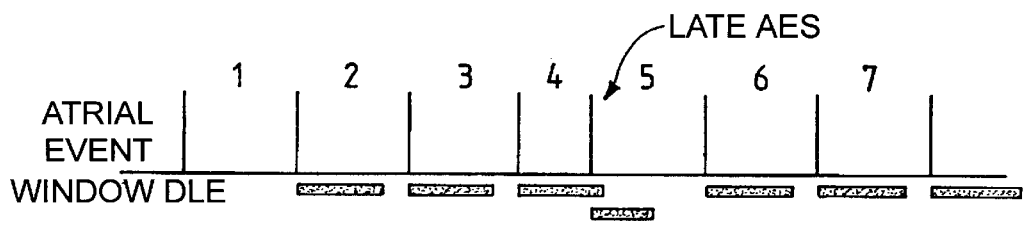
|  | Cycle1 | Cycle2 | Cycle3 | Cycle4 | Cycle5 | Cycle6 | Cycle7 |
|---|---|---|---|---|---|---|---|
| COUPLING INTERVAL FOR ATRIAL DETECTION | 900 | 900 | 900 | 600 | 900 | 900 | 900 |
| AAI |  | 900 | 900 | 900 | 600 | 900 | 900 |
| VALUE OF DLE |  | 737 | 737 | 737 | 550 | 737 | 737 |
| ALGORITHM |  | Active | Active | Inactive | Active | Active | Active |
FIG_4
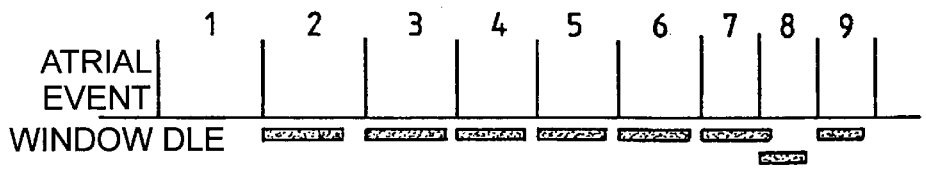
|  | C1 | C2 | C3 | C4 | C5 | C6 | C7 | C8 | C9 |
|---|---|---|---|---|---|---|---|---|---|
| COUPLING INTERVAL FOR ATRIAL DETECTION | 900 | 900 | 800 | 700 | 700 | 700 | 500 | 500 | 500 |
| AAI |  | 900 | 900 | 800 | 700 | 700 | 700 | 500 | 500 |
| VALUE OF DLE |  | 740 | 740 | 675 | 610 | 610 | 610 | 490 | 490 |
| ALGORITHM |  | Active | Active | Active | Active | Active | Inactive | Active | Active |

DETECTION OF LATE ATRIAL EXTRASYSTOLES IN AN ACTIVE IMPLANTABLE MEDICAL DEVICE SUCH AS PACEMAKER DEFIBRILLATOR, CARDIOVERTOR AND/OR MULTISITE DEVICE

FIELD OF THE INVENTION

The present invention relates to "active implantable medical devices" as defined by the Jun. 20, 1990 directive 90/385/CEE of the Council of the European Communities, more particularly to the pacemaker, defibrillator and/or cardiovertor devices, including "multisite" devices, that are able to deliver to the heart low energy stimulation pulses for the treatment of the disorders of the cardiac rate, and even more particularly to the treatment of the disorders of the atrial rate with active implantable medical devices.

BACKGROUND OF THE INVENTION

In connection with the treatment of atrial rate disorders, certain cardiac stimulation algorithms require discriminating between sinusal atrial depolarization and atrial extrasystoles (AES) of an ectopic origin, before engaging in a corrective action.

AES are in general characterized by a relatively short coupling interval (i.e., an interval of time separating two successive atrial events). To detect those AES with a short coupling interval, the known devices use intervals referred to as windows or refractory periods that are started on the detection of an event (an atrial or ventricular event, according to the type of pacemaker). Any atrial activity that is then detected inside (i.e., during) this interval will be regarded as a AES by the software of the pacemaker. The device then will take a suitable action or not, according to the control algorithms provided.

One can thus envisage two such intervals: (1) a fixed window started on a ventricular event, called "PVARP" (post-ventricular atrial refractory period); and (2) a dynamic window started on an atrial event, hereinafter called "DARRP" (dynamic atrial relative refractory period). The atrial event starting the DARRP window also starts the application of an atrio-ventricular delay (AVD) interval.

It happens, however, that AES also occur with a low prematurity, i.e., with a relatively long coupling interval. Such an AES, which will be called hereafter "late AES," can occur after the end of the PVARP or the DARRP window and thus be seen by the pacemaker—incorrectly—as a depolarization of sinusal origin. Taking into account its prematurity, this late AES will be interpreted—still incorrectly—by the pacemaker control algorithm as an acceleration of the sinusal rate of the patient. This will lead the stimulation control algorithm of the pacemaker to take inappropriate actions.

One can take as an example the particular control algorithm known as "physiological overdriving" as described in particular in the EP-A-0 880 979 and its corresponding U.S. application Ser. No. 98US-09/079,333, now U.S. Pat. No. 6,078,836 copending and commonly assigned herewith to ELA Médical, Montrouge, France) the purpose of which is to permanently stimulate the atria after detection of one or more atrial activations of sinusal origin. The pacemaker then increases its stimulation frequency so as to overdrive the otherwise spontaneous rate. But in the event of a late AES, there will result an inopportune increase in the stimulation frequency, which can be badly tolerated by the patient, and in any case is not in conformity with the physiology of the patient.

FIG. 1 shows a ECG strip corresponding to such a situation, where a physiological overdriving algorithm is disturbed by a late AES. In the beginning, the atrial escape interval ("AEI") (i.e., the interval of time, started after a detection or a stimulation in the atrium, at the end of which a stimulation is delivered to the atrium if no spontaneous event is detected) is 780 ms. The overdriving algorithm has calculated on this basis a dynamic window DARRP duration of 585 ms (75% of 780 ms, corresponding to a prematurity rate of AES of 25%). If, as illustrated, a late AES occurs at 600 ms, i.e., with a prematurity of 23%, this late AES will not be recognized as an AES and will instead be seen by the pacemaker as a sinusal atrial depolarization. The reduction in the coupling interval, from 780 to 600 ms, will then be incorrectly interpreted as an acceleration of the sinusal rate, which will cause an abrupt increase in the frequency of atrial stimulation, with the AEI changing from 780 to 550 ms.

The increase of the duration of the PVARP or DARRP windows would not resolve this difficulty, because an excessive lengthening of these windows would be likely to generate a significant number of false positives, i.e., in the event of a spontaneous sinusal acceleration of the atrial rate of the patient, sinusal depolarization would be incorrectly interpreted as an AES, preventing the pacemaker from reacting quickly to the acceleration of the heartbeat rate.

OBJECTS AND SUMMARY OF THE INVENTION

It is, therefore, an object of the present invention to mitigate the aforementioned difficulty, by differentiating the late AES of ectopic origin from spontaneous sinusal accelerations of the patient, and thereby to avoid deluding the control algorithm(s) of the pacemaker by an incorrect interpretation of nature of the atrial depolarization.

For this purpose, the invention thus proposes an improvement to a device of the known type, for example, according to the EP-A-0 880 979 publication mentioned above, including: means for detecting atrial cardiac events; means for applying to the detected atrial events a first window forming an atrial refractory period for the elimination (blanking) of atrial extrasystoles with early or average prematurity, and optionally for the management of the atrio-ventricular delay; and means for reacting to a variation of the sinusal atrial rate detected and filtered by the aforementioned first window.

According to the invention, the foregoing device is improved by also including means for applying to the detected atrial events a second window, distinct from the first window and of a longer duration, forming a relative atrial refractory period for the elimination of the atrial extrasystoles with low prematurity, the duration of this second window being of a variable duration, defined as a fraction of the current average atrial interval; and means for inhibiting temporarily the aforementioned means reacting to a variation of the sinusal atrial rate, in the event of detection of an atrial event inside the second window.

The second window duration, referred to as DLE, can in particular be given by the expression DLE=a *AAI+k; with 0<a<1, for example, a=0.625; a and k being selected so that the current duration of the second window is less than that of the first window. Advantageously, k is positive and selected so that atrial detections occur systematically inside the second window beyond a predetermined level of heart rate, for example, k=175 ms.

The invention applies preferentially in the case where the first window is a window of the dynamic atrial relative refractory period (DARRP) type.

BRIEF DESCRIPTION OF THE DRAWINGS

Other features, characteristic and advantages of the present invention will appear to a person of ordinary skill in the art, in view of the following description, made with reference to the drawings annexed, in which:

FIG. 1 is a representative electrocardiogram ("ECG") showing the way in which a physiological overdriving algorithm can be disturbed by an occurrence of a late AES;

FIG. 2 is a flowchart illustrating the way in which the invention is carried out in accordance with a preferred embodiment of the invention;

FIG. 3 illustrates an application of the invention to the case of an isolated late AES: and FIG. 4 illustrates an application of the invention to the case of a normal sinusal acceleration of the rate of the patient.

DETAILED DESCRIPTION OF THE DRAWINGS

Figure 5:
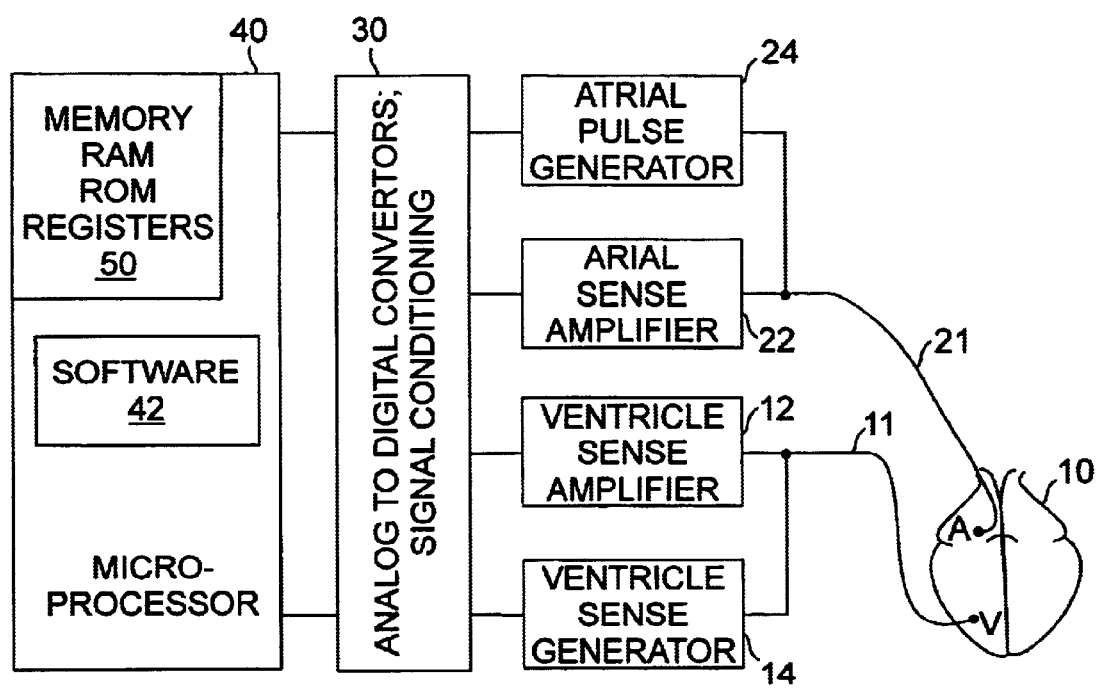
FIG. 5 is a schematic drawing of a device in accordance with the present invention.

As set forth in the background of the invention, recent known pacemakers use a dynamic window DARRP to filter certain AES. But the role of this window DARRP is typically twofold: first, it detects certain AES, and second, it ensures the management of the atrio-ventricular delay (AVD) while avoiding synchronizing the ventricles on fast atrial rates.

Generally, it is not possible to increase the duration of the window DARRP because, on the one hand, it will increase the risk of detection of false positives and, on the other hand, it will seriously disturb the management of the AVD.

The solution suggested by the present invention therefore is to provide an additional interval or window, independent of the DARRP window, having the single function of discriminating the late AES. This additional window will thus be called hereafter "DLE" (detection of late extrasystoles). This window DLE is complementary to, but does not replace, the window DARRP.

The DLE window is frequently determined, i.e., recomputed, ideally at each cycle, similar to the DARRP window. This is done to take account of the current atrial rate. The calculation of the DLE window duration is such that the DLE window is increasingly longer than the DARRP window, provided that the parameter k is positive and that the atrial frequency is below a given threshold.

An atrial detection occurring in the DARRP window will be always regarded as an AES. On the other hand, an atrial detection occurring in the DLE window will not be always regarded as an AES. Indeed, this latter detection can either come from a sinusal acceleration or be a late AES. In the case of such a detection, taking into account this uncertainty, the invention operates to temporarily inhibit the action of the class of algorithms that are based on the atrial sinus rate, i.e., algorithms which react to sinusal atrial activity, such as the aforementioned physiological overdriving algorithm.

The analysis of the events following a detection in the DLE window will make it possible to remove the uncertainty of the nature of the detected atrial event, as follows:

if it is a sinusal acceleration, the new atrial rate will be constant and relatively stable from one cycle to another, so that:
  as long as the DLE window was not recomputed, atrial activity will occur in the DLE window, and the algorithm will continue to be inhibited;
  as soon as the DLE window is recomputed starting from the current rate (thus leading to a shorter value of the window), atrial detections will no longer be in the DLE window, but after the DLE window; the following atrial detections could then rightly be considered as sinusal activity, and the algorithms based on the sinus will then be reactivated.

in the contrary case, if it were a late AES and not a sinusal acceleration, the acceleration of the atrial rate will not be constant: there will thus be a small number of cycles with atrial detection inside the DLE window, during which cycles the algorithms based on the sinus will be inhibited. One will thus avoid activating in an inappropriate way these algorithms.

The flow chart of FIG. 2 illustrates the sequence of the various stages in accordance with a preferred embodiment of the present invention. More precisely, the DLE window has a duration that is calculated according to the current atrial rate (the measurement of this rate at step 210 forms part of the preexistent functionalities of the known pacemakers) as is well known to persons skilled in the art. This window, just like the DARRP window, is initiated at step 220 on any atrial detection for which the pacemaker starts a AVD. The current atrial rate is in particular determined by duration of the atrial-atrial interval average ("AAI") (also called the "PP average"), calculated, for example, over eight cardiac cycles not including an AES.

The DLE window is a dynamic window that is evolutionary according to the atrial rate. Therefore, its performance will be improved if the measurement of the current atrial rate is often updated, by moving apart not taking into account the abnormal cycles. One can take, for example, for AAI the value of the interval of the last atrial cycle if it appears normal (i.e., it does not contain premature events or interference), and in the contrary case, one will take the average of the N last normal cycles (for example, N=8).

The duration, in milliseconds, of the DLE window will advantageously be calculated according to the following relation:

$$DLE = a * AAI + k.$$

The coefficient a (a<1), makes it possible to obtain a DLE window that is shorter than the current atrial rate. A value a=0.625 makes it possible, for example, to detect the AES having a prematurity of at least 37.5%.

The use of constant k is optional. This constant, for example, k=175 ms, lengthens the value of DLE window in manner that, beyond a certain level of heart rate, atrial detections will occur systematically inside the DLE window. This makes it possible to inhibit (i.e. make inactive) in all circumstances the control algorithms based on the sinus, in particular the algorithms of physiological overdriving, each time the atrial frequency rises above a predetermined threshold, regardless of whether the increase is from sinusal acceleration or an AES. Thus, by selecting appropriate values of a and k, a threshold of, for example, 100, 120 or 150 beats per minute, can be set and the ability to inactivate certain algorithms at a certain level of an atrial rate can be provided. In certain configurations, the parameter k can be selected to be a negative value, in which case, there will be no limitation beyond a threshold frequency.

With reference to FIG. 2, once the duration of the DLE window is recomputed at step 220, on each detection of an atrial event EvtA one compares the coupling interval of this event to the value of the DLE window. If detection occurs inside the DLE window, then at step 230 the algorithm based on the sinus is inactivated for (at least) the duration of this cycle. In the contrary case, at step 240, the algorithm is activated normally.

Subsequent detections are treated in the same way, and the DLE window is recomputed according to the current atrial rate as soon as the atrial rate is updated.

FIGS. 3 and 4 illustrate two applications of the invention, respectively in the case of an isolated late AES and in the case of a normal sinusal acceleration. On each of these figures, a chronogram is presented with the successive atrial events and the corresponding calculated DLE windows, as well as a table giving, for each cycle, the values of the coupling interval, the average atrial interval ("AAI"), the duration of the DLE window, and the state, activated or inactivated, of an algorithm based on the sinus. It will be supposed that the duration of the DLE window is calculated in accordance with the expression DLE=0.625* AAI+175, and that the value of AAI is updated at each cycle.

In the case of FIG. 3, the fourth illustrated cycle ends in a late AES, with a coupling interval of 600 ms. The duration of the DLE window calculated for the current rate (constant normal coupling interval of 900 ms) being of 737 ms with the numerical data higher indicated above, the AES occurs inside the DLE window, which causes the system to inhibit the algorithm based on the sinus for that cycle. At the following cycle (Cycle 5), the coupling interval has the value (900 ms) which it had before, the atrial event occurs out of the DLE window (which has been recomputed at 550 ms). This causes the system to reactivate the algorithm, thus restoring the operation of pacemaker to its former normal state.

In the case of FIG. 4, on the other hand, the atrial frequency increases regularly because of a normal sinusal acceleration. During the first six cycles, the value of the DLE window adapts to this acceleration, and the algorithm based on the sinus remains activated.

During the seventh cycle, the acceleration is a little stronger, leading to a fast reduction in the coupling interval. The eighth detected atrial event (coupling interval 500 ms) then occurs inside the DLE window (having a duration 610 ms) and, for safety due to the uncertainty of origin of the detected event, the algorithm based on the sinus is inactivated.

The analysis of the following atrial event, which reveals the maintenance of the sustained atrial rate, makes it possible to remove the uncertainty by dismissing the assumption of a late AES. The DLE window having been reduced (from 610 to 490 ms), this new event, as compared to the preceding event, presents a coupling interval of 500 ms, and occurs out of the DLE window. This causes the system to reactivate the algorithm, which will then be able to take, if necessary, the suitable actions corresponding to sinusal acceleration.

As would be understood by a person of ordinary skill in the art, the foregoing may be implemented in an active implantable medical device by use of discrete circuits (analog and/or digital circuits) or alternatively, by a microprocessor based device operating under software control. Indeed, software suitable to perform the above described operations is believed to be easily written by and within the abilities of a person of ordinary skill in the art and may be stored in suitable memory, e.g., ROM, or in firmware.

As illustrated in FIG. 5, the detection of atrial and ventricular complexes and the measuring of the amplitude of these atrial and ventricular complexes are performed by conventional electronic means, e.g., digital microprocessor controlled devices having sense amplifiers, e.g., ventricle sense amplifier 12 and atrial sense amplifier 22 analog to digital conversion circuits 30 and microprocessor 40 with software 42 and suitable memory and registers 50 for data processing and manipulation. These devices also include an atrial pulse generator 24 and a ventricle pulse generator 14 for stimulating the atrium and ventricle under device control. The present invention is preferably implemented under software control, and occurs following acquisition of the cardiac electric signals by a conventional sense amplifier, e.g., by sensing electrical activity in the heart 10 atrial A and ventricle V using cardiac leads 11 and 21, preferably after the acquired signals have been conditioned and converted to digital form in the usual manner. Representative electronic circuits algorithm are those found in the series of dual chamber pacemakers, available from ELA Medical, Montrouge, France, offered under the CHORUS trademark. The method also used could be performed using, and the apparatus constructed of, discrete circuitry, if desired.

One skilled in the art will appreciate that the present invention can be practiced by other than the described embodiments, which are presented for the purposes of illustration and not of limitation.

We claim:

1. An active implantable medical device, having a means for delivering to the heart pulses of low energy for the treatment of the disorders of the cardiac rate, including: means for detecting atrial cardiac events (EvtA) and determining an average atrial-atrial interval; means for providing a first window in response to each atrial event having a first duration for discriminating atrial extrasystoles with earlier or average prematurity; means for applying a detected atrial event to said first window and determining a sinusal atrial rate from atrial events; means for reacting to a variation of the determined sinusal atrial rate, wherein the improvement comprises:

means for providing a second window in response to each atrial event, having a second duration (DLE) longer than said first duration, forming an atrial refractory period for discriminating late atrial extrasystoles with low prematurity, the second duration being a variable duration, defined as a fraction of the determined average atrial-atrial interval (AAI);

means for applying said detected atrial event to said second window; and means for temporarily inhibiting said reacting means, in response to a detection of an atrial event inside the second window.

2. The device of claim 1, wherein the second duration of the second window is given by the expression:

$$DLE = a*AAI + K,$$

with $0 < a < 1$, a and being selected so that the current duration of the second window is less than AAI.

3. The device of claim 2, wherein a=0.625.

4. The device of claim 2, wherein k is a positive value selected so that atrial detections occur systematically inside the second window beyond a predetermined heart rate level.

5. The device of claim 4, wherein k=175 ms.

6. The device of claim 1, wherein the first window is a dynamic atrial relative refractory period window.

7. The device of claim 1, further comprising means, responsive to temporarily inhibiting said reacting means and to detecting a subsequent detected atrial event outside the second window, for uninhibiting said reacting means for said subsequent atrial event.

* * * * *